United States Patent
Hasegawa

(10) Patent No.: US 10,386,633 B2
(45) Date of Patent: Aug. 20, 2019

(54) VIRTUAL OBJECT DISPLAY SYSTEM, AND DISPLAY CONTROL METHOD AND DISPLAY CONTROL PROGRAM FOR THE SAME

(71) Applicant: FUJIFILM Corporation, Tokyo (JP)

(72) Inventor: Yu Hasegawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 15/702,108

(22) Filed: Sep. 12, 2017

(65) Prior Publication Data

US 2018/0011317 A1 Jan. 11, 2018

Related U.S. Application Data

(63) Continuation of application No. PCT/JP2016/053950, filed on Feb. 10, 2016.

(30) Foreign Application Priority Data

Mar. 13, 2015 (JP) ................... 2015-050225

(51) Int. Cl.
*G09G 5/00* (2006.01)
*G02B 27/01* (2006.01)
(Continued)

(52) U.S. Cl.
CPC ............ *G02B 27/0101* (2013.01); *A61B 6/02* (2013.01); *A61B 6/03* (2013.01); *G02B 27/017* (2013.01);
(Continued)

(58) Field of Classification Search
CPC ........... G06F 3/033; G06F 3/048; G09G 5/08; G09G 5/00; G09G 5/10; G09G 5/02; G06K 9/00
See application file for complete search history.

(56) References Cited

U.S. PATENT DOCUMENTS 6,020,891 A 2/2000 Rekimoto
2006/0227151 A1* 10/2006 Bannai .................... A63F 13/00
345/633

(Continued)

FOREIGN PATENT DOCUMENTS

JP 10-51711 A 2/1998
JP 2006-293604 A 10/2006
(Continued)

OTHER PUBLICATIONS

Japanese Office Action dated Jan. 9, 2018, for corresponding Japanese Application No. 2015-050225, with English translation.

(Continued)

*Primary Examiner* — Pegeman Karimi
(74) *Attorney, Agent, or Firm* — Birch, Stewart, Kolasch & Birch, LLP

(57) ABSTRACT

A virtual object display system includes a plurality of head-mounted displays 1 each having a virtual object acquisition unit 22 that acquires a virtual object, a display information acquisition unit 23 that acquires display information used to display the virtual object, and a display control unit 24 that causes a display unit to display the virtual object on the basis of the display information, and enables switching between of first display control for causing the virtual object to be displayed on the basis of display information acquired by each of the plurality of head-mounted displays 1 and second display control for causing the virtual object having an identical orientation to an orientation of the virtual object displayed on the basis of display information acquired by another head-mounted display 1 to be displayed.

19 Claims, 9 Drawing Sheets

(51) Int. Cl.
*A61B 6/02* (2006.01)
*A61B 6/03* (2006.01)
*G06F 3/0481* (2013.01)
*G09G 5/36* (2006.01)
*G06F 3/147* (2006.01)
*G09G 3/00* (2006.01)
*G06Q 50/22* (2018.01)

(52) U.S. Cl.
CPC ........ *G06F 3/0481* (2013.01); *G06F 3/04815* (2013.01); *G06F 3/147* (2013.01); *G09G 3/002* (2013.01); *G09G 3/003* (2013.01); *G09G 5/00* (2013.01); *G09G 5/36* (2013.01); *G02B 2027/0134* (2013.01); *G02B 2027/0138* (2013.01); *G02B 2027/0141* (2013.01); *G06Q 50/22* (2013.01)

(56) References Cited

U.S. PATENT DOCUMENTS

| | | | | |
|---|---|---|---|---|
| 2011/0029903 | A1* | 2/2011 | Schooleman | G06F 3/011 715/764 |
| 2012/0249416 | A1* | 10/2012 | Maciocci | G06F 3/011 345/156 |
| 2012/0269388 | A1 | 10/2012 | Jiang et al. | |
| 2013/0243275 | A1* | 9/2013 | Baym | G06F 19/00 382/128 |
| 2016/0103326 | A1* | 4/2016 | Kimura | G02B 27/017 345/690 |
| 2017/0318235 | A1* | 11/2017 | Schneider | G02B 27/2228 |

FOREIGN PATENT DOCUMENTS

| | | |
|---|---|---|
| JP | 2010-170316 A | 8/2010 |
| JP | 2014-514653 A | 6/2014 |
| JP | 2014-522007 A | 8/2014 |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2016/053950, dated Sep. 28, 2017, with an English translation of the Written Opinion.

International Search Report (Form PCT/ISA/210) for International Application No. PCT/JP2016/053950, dated Mar. 22, 2016, with an English translation.

* cited by examiner

VIRTUAL OBJECT DISPLAY SYSTEM, AND DISPLAY CONTROL METHOD AND DISPLAY CONTROL PROGRAM FOR THE SAME

CROSS-REFERENCE TO RELATED APPLICATIONS

This application is a Continuation of PCT International Application No. PCT/JP2016/053950 filed on Feb. 10, 2016, which claims priority under 35 U.S.C § 119(a) to Patent Application No. 2015-050225 filed in Japan on Mar. 13, 2015, all of which are hereby expressly incorporated by reference into the present application.

BACKGROUND OF THE INVENTION

1. Field of the Invention

The present invention relates to a virtual object display system including a plurality of virtual object display devices each of which displays a virtual object by using augmented reality and to a display control method and a non-transitory computer readable recording medium storing a display control program for the same.

2. Description of the Related Art

In recent years, there have been proposed display systems using augmented reality that enables a virtual object to appear to exist in a real space by superimposing the virtual object on a real-time background video image obtained by imaging the real space and by displaying the resultant combined image on a display device, such as a head-mounted display. In such systems, a marker that defines a position at which the virtual object is to be displayed is placed in the real space. The marker is then detected from the background video image that is obtained by imaging the real space. Further, the position at which and the size and orientation in which the virtual object is to be displayed is determined in accordance with the position, size, and orientation of the detected marker, and the virtual object is displayed at the determined display position in the determined size and orientation on the display device. An image, for example, a two-dimensional barcode, is used as such a marker. Techniques that enable the use of an LED (Light Emitting Diode) or an operator's finger as the marker have also been proposed.

In addition, in the medical field, participants of a surgery gather together prior to the surgery and hold a pre-surgery conference for explaining the surgery. During such a pre-surgery conference, augmented reality has come into use in recent years to display a target site of the surgery and to simulate the surgery. For example, a surgery-target site is extracted from a three-dimensional image obtained from sectional images such as CT (Computed Tomography) images or MRI (magnetic resonance imaging) images, and a virtual object is generated based on a three-dimensional image of the surgery-target site. The virtual object is then displayed in actual size by using augmented reality. By using the displayed virtual object, an explanation is given to the participants of the pre-surgery conference by the surgeon who is a representative of the conference and the surgical procedure is simulated. At that time, all the participants of the conference can proceed with the conference while viewing a common virtual object by wearing display devices, such as head-mounted displays.

SUMMARY OF THE INVENTION

However, in the case where a common virtual object is observed by a plurality of people including the surgeon and the participants as described above, each of the participants needs to move to an easy-to-view position when the participant desires to view a site that is difficult to view unless observation is made from a particular direction and when an assistant desires to view the virtual object in the field of view from the same direction as the direction of the surgeon. In addition, in the case where there are many participants of the pre-surgery conference, it is difficult for all the participants to view the virtual object from the same angle.

Although observation of a common virtual object by a plurality of people has been proposed in Japanese Unexamined Patent Application Publication (Translation of PCT Application) No. 2014-522007, a method for solving the aforementioned issues has not been proposed.

In view of the circumstance described above, the present invention aims to provide a virtual object display system that allows, in the case where a common virtual object is observed by a plurality of people, each of the observers to observe the virtual object from an appropriate direction according to a situation without moving and to provide a display control method and a non-transitory computer readable recording medium storing a display control program for the same.

A virtual object display system according to an aspect of the present invention includes a plurality of virtual object display devices each having a virtual object acquisition unit that acquires a virtual object, a display information acquisition unit that acquires display information including position information used to display the virtual object and orientation information used to display the virtual object, and a display control unit that causes a display unit to display the virtual object on the basis of the display information, in which the display control unit of each of the plurality of virtual object display devices is capable of switching between first display control for causing the virtual object to be displayed on the basis of display information acquired by the display information acquisition unit of the virtual object display device and second display control for causing the virtual object having an identical orientation to an orientation of the virtual object displayed on the basis of display information acquired by the display information acquisition unit of another virtual object display device among the plurality of virtual object display devices to be displayed.

In addition, in the virtual object display system according to the aspect of the present invention, in a case where the display information acquired by the display information acquisition unit of the other virtual object display device is changed after switching to the second display control, the display control unit of each of the plurality of virtual object display devices can change display of the virtual object on the basis of the changed display information.

In addition, in the virtual object display system according to the aspect of the present invention, the display information can include size information used to display the virtual object, and in a case where the display information acquired by the display information acquisition unit of the other virtual object display device is changed after switching to the second display control, the display control unit of each of the plurality of virtual object display devices can change display of the virtual object on the basis of the changed display information excluding the size information.

In addition, in the virtual object display system according to the aspect of the present invention, the display control unit of each of the plurality of virtual object display devices can change display of the virtual object in accordance with a change in the display information acquired by the display information acquisition unit of the virtual object display device after switching to the second display control.

In addition, in the virtual object display system according to the aspect of the present invention, each of the plurality of virtual object display devices can include an imaging unit that acquires a background video image, and the display control unit of each of the plurality of virtual object display devices, in a case of the first display control, can cause the background video image acquired by the imaging unit of the virtual object display device and the virtual object to be displayed and superimposed, and, in a case of the second display control, is capable of switching between third display control for causing the background video image acquired by the imaging unit of the virtual object display device and the virtual object having the identical orientation to be displayed and superimposed and fourth display control for causing the background video image acquired by the imaging unit of the other virtual object display device and the virtual object having the identical orientation to be displayed and superimposed.

In addition, the virtual object display system according to the aspect of the present invention can include a specified position information acquisition unit that acquires, after a position on the virtual object displayed on a virtual object display device among the plurality of virtual object display devices is specified by a user, position information on the specified position, in which the display control unit of the virtual object display devices other than the virtual object display device associated with the user who has specified the position on the virtual object can cause an image representing the specified position to be displayed on the virtual object on the basis of the position information acquired by the specified position information acquisition unit.

In addition, the virtual object display system according to the aspect of the present invention can include a switching instruction accepting device that accepts a switching instruction for switching between the first display control and the second display control, in which the display control unit of each of the plurality of virtual object display devices can switch between the first display control and the second display control in accordance with the switching instruction accepted by the switching instruction accepting device.

In addition, in the virtual object display system according to the aspect of the present invention, the display information acquisition unit can acquire the display information from a marker image obtained by imaging a marker used to display the virtual object.

In addition, the virtual object can be a three-dimensional image.

In addition, the three-dimensional image can be a three-dimensional medical image.

In addition, the display unit can be an eyeglass-shaped display device.

A display control method for a virtual object display system according to another aspect of the present invention is a display control method for a virtual object display system, the virtual object display system including a plurality of virtual object display devices each of which acquires a virtual object, acquires display information including position information used to display the virtual object and orientation information used to display the virtual object, and causes a display unit to display the virtual object on the basis of the display information, in which each of the plurality of virtual object display devices switches between first display control for causing the virtual object to be displayed on the basis of display information acquired by the virtual object display device and second display control for causing the virtual object having an identical orientation to an orientation of the virtual object displayed on the basis of display information acquired by another virtual object display device among the plurality of virtual object display devices to be displayed.

A non-transitory computer readable recording medium storing a display control program for a virtual object display system according to still another aspect of the present invention is a non-transitory computer readable recording medium storing a display control program for a virtual object display system, the virtual object display system including a plurality of virtual object display devices each of which acquires a virtual object, acquires display information including position information used to display the virtual object and orientation information used to display the virtual object, and causes a display unit to display the virtual object on the basis of the display information, the display control program causing each of the plurality of virtual object display devices to execute a process of switching between first display control for causing the virtual object to be displayed on the basis of display information acquired by the virtual object display device and second display control for causing the virtual object having an identical orientation to an orientation of the virtual object displayed on the basis of display information acquired by another virtual object display device among the plurality of virtual object display devices to be displayed.

With the virtual object display system and the display control method and the non-transitory computer readable recording medium storing the display control program for the same according to the aspects of the present invention, when a common virtual object is displayed on a plurality of virtual object display devices, first display control for causing the virtual object to be displayed on the basis of display information acquired by each of the plurality of virtual object display devices and second display control for causing the virtual object having an identical orientation to an orientation of the virtual object displayed on the basis of display information acquired by another virtual object display device to be displayed are switched between. Thus, the first display control that enables observation of the common virtual object from individual directions in which the respective observers are present and the second display control that enables the other observers to observe the virtual object from the same direction as the direction in which, for example, a surgeon views the virtual object can be switched between. Therefore, each observer can observe the virtual object from an appropriate direction according to a situation without moving.

DESCRIPTION OF THE PREFERRED EMBODIMENTS

Figure 1:
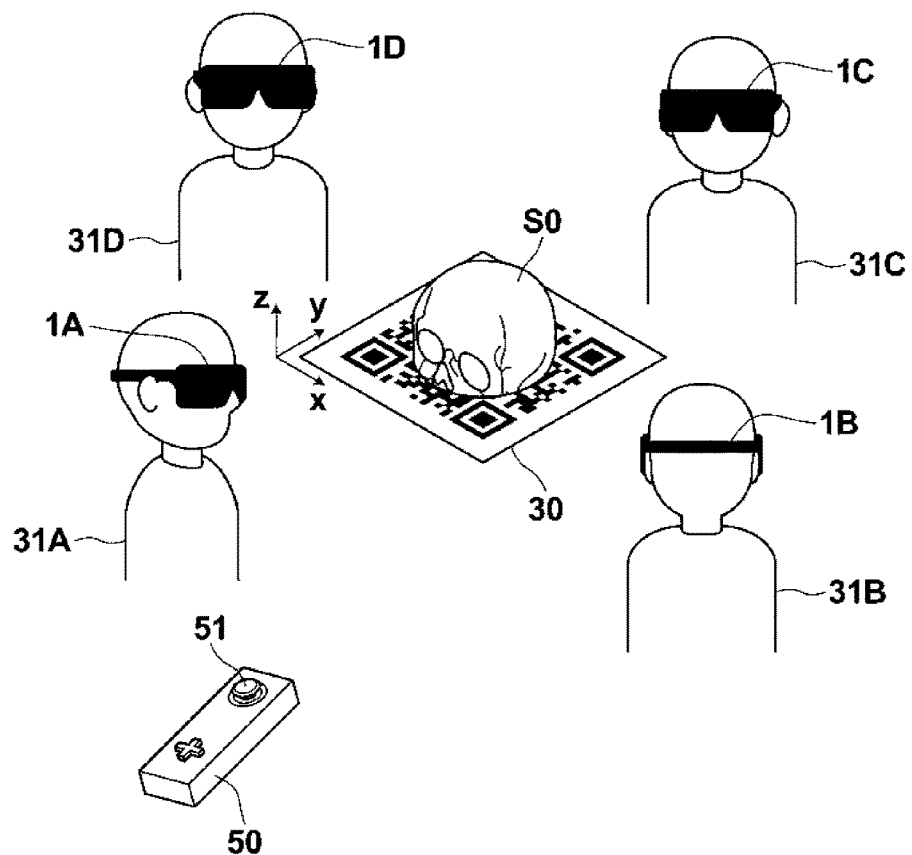
FIG. 1 is a diagram for describing a circumstance where an embodiment of a virtual object display system according to an aspect of the present invention is used.

An embodiment of a virtual object display system according to an aspect of the present invention will be described below with reference to the drawings. FIG. 1 is a diagram for describing a circumstance where a virtual object display system according to this embodiment is used.

The virtual object display system displays a three-dimensional image of a target of a surgery as a virtual object by using augmented reality during a pre-surgery conference. Specifically, the virtual object display system generates, as a virtual object, a three-dimensional image of a target of a surgery from a three-dimensional image obtained by imaging a subject. Then, during a pre-surgery conference, participants of the surgery wear respective head-mounted displays (hereinafter, abbreviated as HMDs) 1A to 1D and display a virtual object S0 on the respective HMDs 1A to 1D. In this way, the virtual object display system is used in a circumstance where the participants receive various explanations regarding the surgery from a surgeon who is a representative of the pre-surgery conference. Note that each of the HMDs 1A to 1D corresponds to a virtual object display device according to an aspect of the present invention.

It is assumed in this embodiment that 31A illustrated in FIG. 1 represents the surgeon and 31B to 31D illustrated in FIG. 1 represent participants of the surgery other than the surgeon. It is also assumed in this embodiment that the surgeon 31A has a switching controller 50 used to switch between a normal mode and a sharing mode described later. This switching controller 50 corresponds to a switching instruction accepting device according to an aspect of the present invention.

Figure 2:
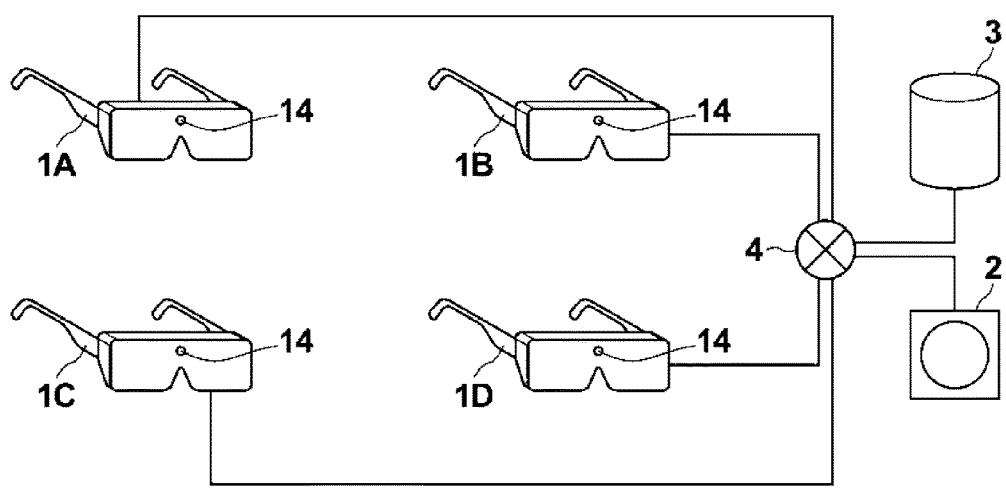
FIG. 2 is a hardware configuration diagram illustrating the overview of the embodiment of the virtual object display system according to the aspect of the present invention.

FIG. 2 is a hardware configuration diagram illustrating the overview of the virtual object display system according to this embodiment. As illustrated in FIG. 2, the virtual object display system according to the embodiment includes the four HMDs 1A to 1D, a three-dimensional imaging apparatus 2, and an image storage server 3. The four HMDs 1A to 1D, the three-dimensional imaging apparatus 2, and the image storage server 3 are connected to one another to be able to perform communication via a network 4. Further, it is assumed in the following description that the four HMDs 1A to 1D are sometimes represented by HMDs 1.

In addition, information can be exchanged among the HMDs 1A to 1D via the network 4. Further, the HMDs 1A to 1D and the switching controller 50 are configured to be able to perform wireless communication. A mode switching signal output from the switching controller 50 is received by the HMDs 1A to 1D via wireless communication.

The three-dimensional imaging apparatus 2 is an apparatus that images a surgery-target site of a subject to generate a three-dimensional image V0 representing that site. Specifically, the three-dimensional imaging apparatus 2 is an apparatus, such as a CT apparatus, an MRI apparatus, or a PET (Positron Emission Tomography) apparatus. The three-dimensional image V0 generated by this three-dimensional imaging apparatus 2 is transmitted to and stored in the image storage server 3. Note that, in this embodiment, the CT apparatus is used as the three-dimensional imaging apparatus 2, the head which is the target of the surgery is imaged by the CT apparatus, and the three-dimensional image V0 of the head is generated.

The image storage server 3 is a computer that stores and manages various kinds of data. The image storage server 3 includes a mass external storage device and database management software. The image storage server 3 communicates with other devices via the network 4, which is wired or wireless, to transmit and receive image data or the like. Specifically, the image storage server 3 acquires, via the network 4, image data of the three-dimensional image V0 generated by the three-dimensional imaging apparatus 2 and stores and manages the image data on a recording medium, such as the mass external storage device. Note that the storage format of image data and communication between the devices via the network 4 are based on a protocol, such as DICOM (Digital Imaging and Communication in Medicine).

The HMD 1 includes a computer, and a virtual object display program according to an aspect of the present invention is installed on the computer. The virtual object display program is installed in a memory of the HMD 1. Alternatively, the virtual object display program is stored in a storage device of a server computer connected to the network or a network storage to be accessible from the outside and is downloaded to and installed on the HMD 1 in response to a request.

Figure 3:
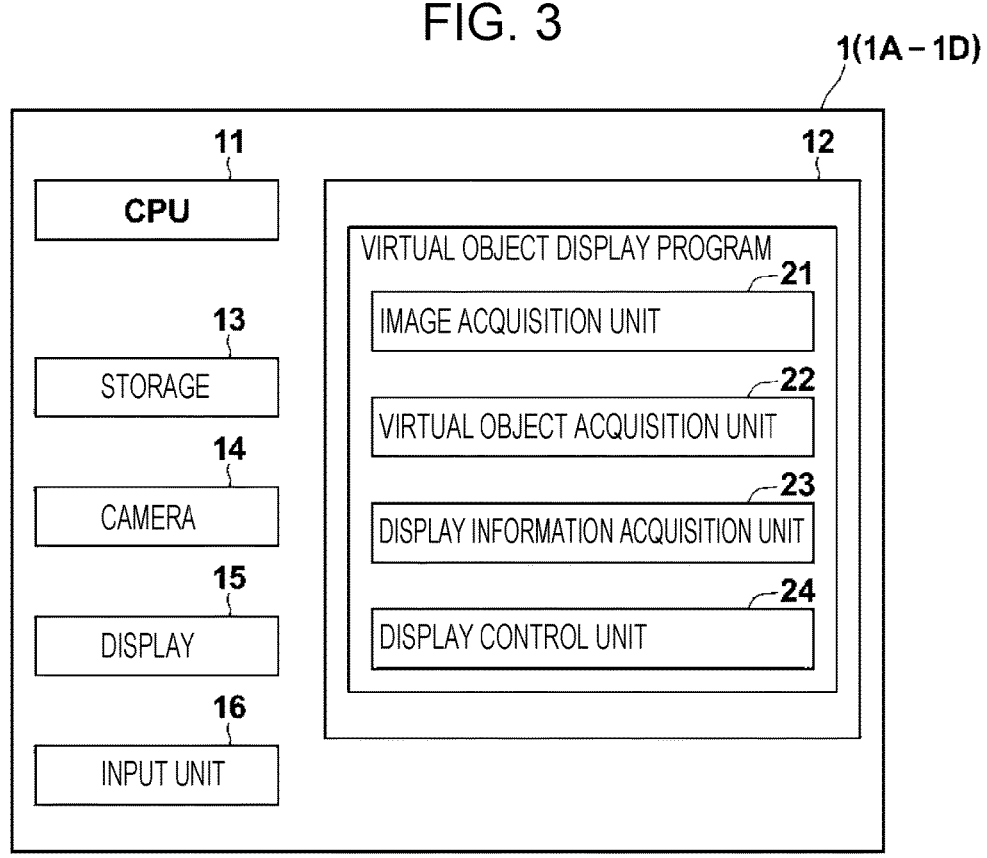
FIG. 3 is a block diagram illustrating a schematic configuration of a head-mounted display which is a virtual object display device.

FIG. 3 is a block diagram illustrating a schematic configuration of the HMD 1 which is a virtual object display device implemented by installation of the virtual object display program. As illustrated in FIG. 3, the HMD 1 includes a CPU (Central Processing Unit) 11, a memory 12, a storage 13, a camera 14, a display 15, and an input unit 16. Note that the camera 14 corresponds to an imaging unit according to an aspect of the present invention, and the display 15 corresponds to a display unit according to an aspect of the present invention. The camera 14 and the display 15 may be provided in a head-worn portion of the HMD 1, and the memory 12, the storage 13, and the input unit 16 may be provided separately from the head-worn portion.

The storage 13 stores various kinds of information including the three-dimensional image V0 acquired from the image storage server 3 via the network 4 and images generated by processing performed by the HMD 1.

The camera 14 includes a lens, a CCD (Charge Coupled Device) imaging device or the like, and an image processing unit that performs processing to improve the image quality of an acquired image. As illustrated in FIG. 2, the camera 14 is attached to the HMD 1 so that, when each of the surgeon 31A and the participants 31B to 31D wears the HMD 1, the wearer's field of view matches the imaging range of the camera 14. That is, the camera 14 is attached to the HMD 1 to be located at a portion of the HMD 1 corresponding to the center between the eyes of the wearer. Thus, when each of the surgeon 31A and the participants 31B to 31D wears the HMD 1, the camera 14 captures an image corresponding to the wearer's field of view. In this way, a video image of the real space viewed by each wearer is acquired as a background video image B0. The background video image B0 is a motion picture having a predetermined frame rate.

The display 15 includes a liquid crystal panel or the like for displaying the background video image B0 and a virtual object S0. Note that the display 15 includes a display unit for the left eye and a display unit for the right eye of the wearer of the HMD 1.

The input unit 16 consists of, for example, buttons and is provided at a predetermined position of the exterior of the HMD 1.

In addition, the memory 12 stores the virtual object display program. As a result of the CPU 11 executing the virtual object display program, an image acquisition unit 21, a virtual object acquisition unit 22, a display information acquisition unit 23, and a display control unit 24 illustrated in FIG. 3 function.

The image acquisition unit 21 acquires the three-dimensional image V0 and the background video image B0 that is captured by the camera 14. In the case where the three-dimensional image V0 is already stored in the storage 13, the image acquisition unit 21 may acquire the three-dimensional image V0 from the storage 13.

The virtual object acquisition unit 22 generates, as the virtual object S0, an image representing a three-dimensional shape of the head which is the surgery-target site. Specifically, the virtual object acquisition unit 22 generates, as the virtual object S0, a projection image obtained by projecting the image representing the three-dimensional shape of the head onto a projection plane determined by display information described later. Herein, for example, a known volume rendering technique or the like is used as the specific projection method. Note that the virtual object generation method is not limited to this technique, and other known techniques can be used.

In addition, a virtual object generation device, not illustrated, may generate the virtual object S0 from the three-dimensional image V0 and may store the virtual object S0 in the image storage server 3. In this case, the virtual object acquisition unit 22 acquires the virtual object S0 from the image storage server 3.

Figure 4:
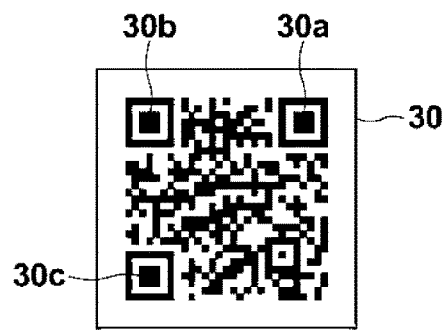
FIG. 4 is a diagram illustrating an example of a marker.

The display information acquisition unit 23 acquires, from the background video image B0, display information representing the position at which and the size and orientation in which the virtual object S0 is to be displayed. In this embodiment, the display information acquisition unit 23 acquires the display information from a marker image that is included in the background video image B0 as a result of imaging a marker used to display the virtual object and that represents the marker. FIG. 4 is a diagram illustrating the marker used in this embodiment. As illustrated in FIG. 4, a marker 30 is created by sticking a two-dimensional barcode to a plate. Note that the marker 30 may be a two-dimensional barcode printed on a sheet. The marker 30 is placed at a place where a pre-surgery conference is held as illustrated in FIG. 1. The surgeon 31A and the participants 31B to 31D wear the HMDs 1A to 1D, respectively. In each of the HMDs 1A to 1D, the background video image B0 acquired by the camera 14 is displayed on the display 15. The surgeon 31A and the participants 31B to 31D turn their eyes toward the marker 30 so that the background video image B0 displayed on the display 15 includes a marker image which is an image of the marker 30.

Figure 5:
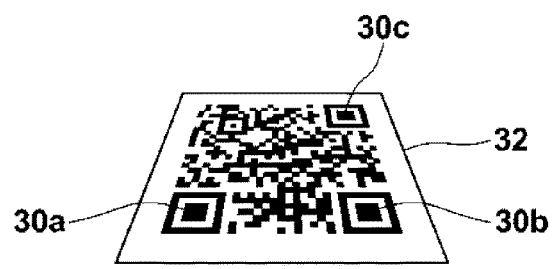
FIG. 5 is a diagram illustrating a marker image extracted from a background video image.

The display information acquisition unit 23 extracts the marker image representing the marker 30 from the background video image B0. FIG. 5 is a diagram illustrating a marker image 32 extracted from the background video image B0. The marker image 32 illustrated in FIG. 5 is an image acquired by the HMD 1A of the surgeon 31A. As illustrated in FIG. 4, the two-dimensional barcode of the marker 30 includes three reference points 30a to 30c. The display information acquisition unit 23 detects the reference points 30a to 30c in the extracted marker image 32. The display information acquisition unit 23 then determines the position at which and the size and orientation in which the virtual object S0 is to be displayed on the basis of the positions of the detected reference points 30a to 30c and intervals between the reference points.

In this embodiment, a position where the reference points 30a and 30b appear to be side by side is defined as the front position with respect to which the virtual object S0 is to be displayed in a normal mode. Thus, by detecting the positions of the reference points 30a and 30b in the marker image 32, a rotation position of the virtual object S0 from the front position with respect to an axis (hereinafter, referred to as a z-axis) perpendicular to the marker 30 can be determined. In addition, the size in which the virtual object S0 is to be displayed can be determined based on a difference of a distance between the reference points 30a and 30b from a predetermined reference value. Further, a rotation position of the virtual object S0 from a reference position with respect to two axes (hereinafter, referred to as an x-axis and a y-axis) that are perpendicular to the z-axis, that is, the orientation, can be determined based on a difference of a triangle having the reference points 30a to 30c as the vertices from a reference shape. The display information acquisition unit 23 outputs the determined position, size, and orientation of the virtual object S0 as the display information.

The display control unit 24 defines a projection plane onto which the virtual object S0 is to be projected and projects the virtual object S0 onto the projection plane by using the display information. The display control unit 24 also superimposes the projected virtual object S0 on the background video image B0 and displays the resultant combined image on the display 15. FIG. 1 schematically illustrates the display state of the virtual object S0 displayed at the place where the pre-surgery conference is held. As illustrated in FIG. 1, each of the surgeon 31A and the participants 31B to 31D can observe, by using the display 15, the state where a three-dimensional image of the head having the size and orientation according to their position is displayed as the virtual object S0 on the marker 30 that exists in the real space.

Note that the display control unit 24 displays the virtual object S0 on the display unit for the left eye and the display unit for the right eye of the display 15 such that the virtual object S0 has parallax. With this configuration, the surgeon 31A and the participants 31B to 31D can stereoscopically view the virtual object S0.

In addition, the surgeon 31A and the participants 31B to 31D can change the orientation of the virtual object S0 displayed on the display 15 by rotating or inclining the marker 30 with respect to the z-axis in this state.

Now, a situation is assumed where the surgeon 31A stands towards the front position of the virtual object S0, the participant 31C stands on the opposite side of the surgeon 31A, the participant 31B stands on the right side of the surgeon 31A, and the participant 31D stands on the left side of the surgeon 31A as illustrated in FIG. 1, for example. In this case, the participant 31C observes the rear side of the virtual object S0 of the head, the participant 31B observes the left side of the virtual object S0 of the head, and the participant 31D observes the right side of the virtual object S0 of the head.

Figure 6:
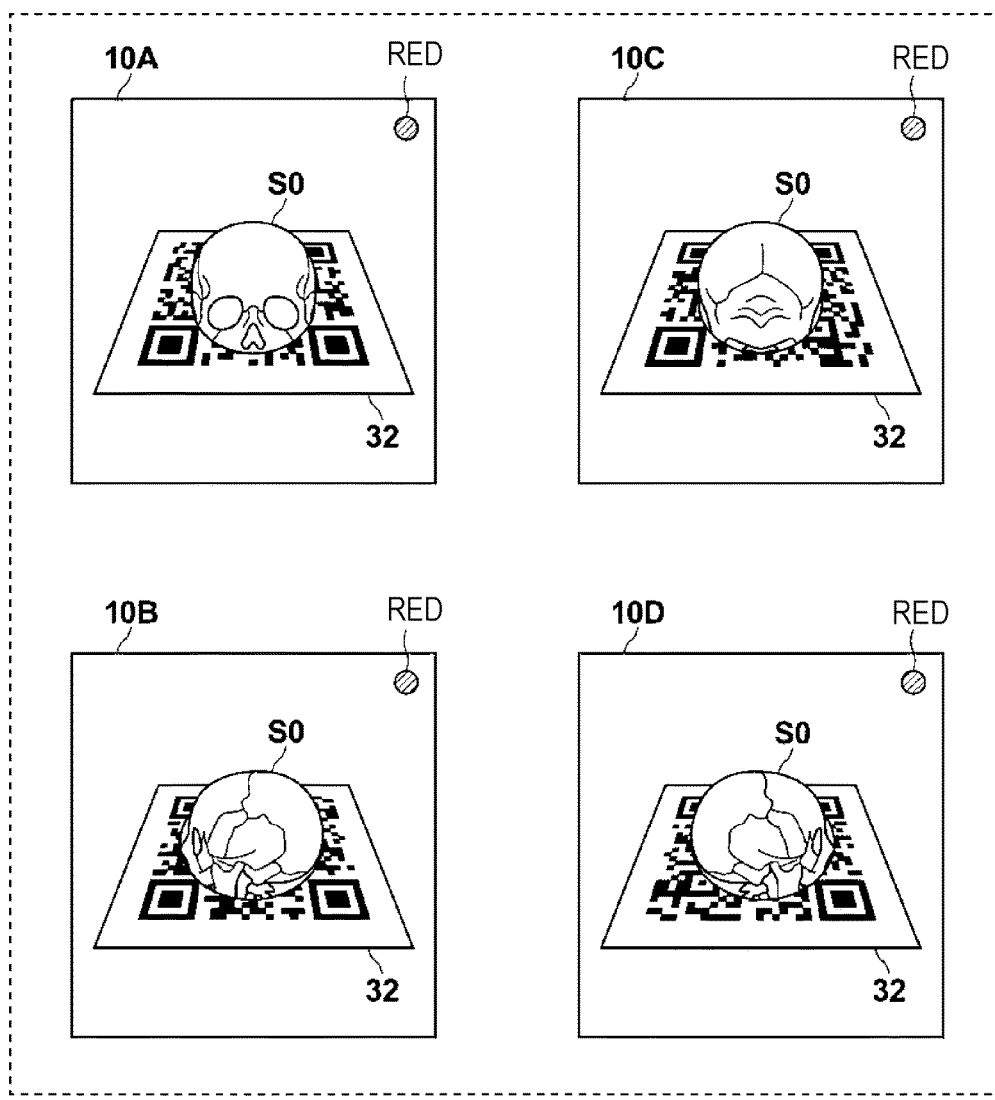
FIG. 6 is a diagram illustrating display states of a virtual object displayed on individual head-mounted displays in a normal mode.

10A in FIG. 6 illustrates the state of the virtual object S0 displayed on the display 15 of the HMD 1A of the surgeon 31A. 10B in FIG. 6 illustrates the state of the virtual object S0 displayed on the display 15 of the HMD 1B of the participant 31B. 10C in FIG. 6 illustrates the state of the virtual object S0 displayed on the display 15 of the HMD 1C of the participant 31C. 10D in FIG. 6 illustrates the state of the virtual object S0 displayed on the display 15 of the HMD 1D of the participant 31D.

As illustrated in FIG. 6, the virtual object S0 is displayed on the respective displays 15 of the surgeon 31A and the participants 31B to 31D in respective orientations according to respective positional relationships between the marker 30 (marker image 32) and the surgeon 31A and the participants 31B to 31D. In this embodiment, this type of the display state of the virtual object S0 is referred to as a normal mode. Note that, in the normal mode, a red circular mark indicating that the mode is currently set in the normal mode is displayed at the upper right corner of the display 15 of each of the surgeon 31A and the participants 31B to 31D as illustrated in FIG. 6.

As described above, there are cases where the participants 31B to 31D desire to view a site that is difficult to view unless observation is made from a particular direction and where the participants 31B to 31D desire to view the site in the field of view from the same direction as the direction of the surgeon 31A during a pre-surgery conference. However, each of the participants 31B to 31D needs to move to an easy-to-view position in the above-described display state of the normal mode using the marker 30. In addition, in the case where there are many participants of the pre-surgery conference, it is difficult for all the participants to view the virtual object from the same angle.

Accordingly, this embodiment is configured to enable switching to a sharing mode in which the virtual object S0 having the same orientation is displayed on the displays 15 of the HMDs 1A to 1D so that all the surgeon 31A and the participants 31B to 31D can observe the virtual object S0 having the same orientation. Note that the normal mode described above corresponds to first display control according to an aspect of the present invention, and the sharing mode corresponds to second display control according to an aspect of the present invention. Switching from the normal mode to the sharing mode will be described in detail below.

Switching from the normal mode to the sharing mode is performed by using the switching controller 50 illustrated in FIG. 1. Specifically, when the surgeon 31A presses a mode switching button 51 of the switching controller 50, a switching instruction signal for switching from the normal mode to the sharing mode is output from the switching controller 50 to the HMDs 1A to 1D.

Figure 7:
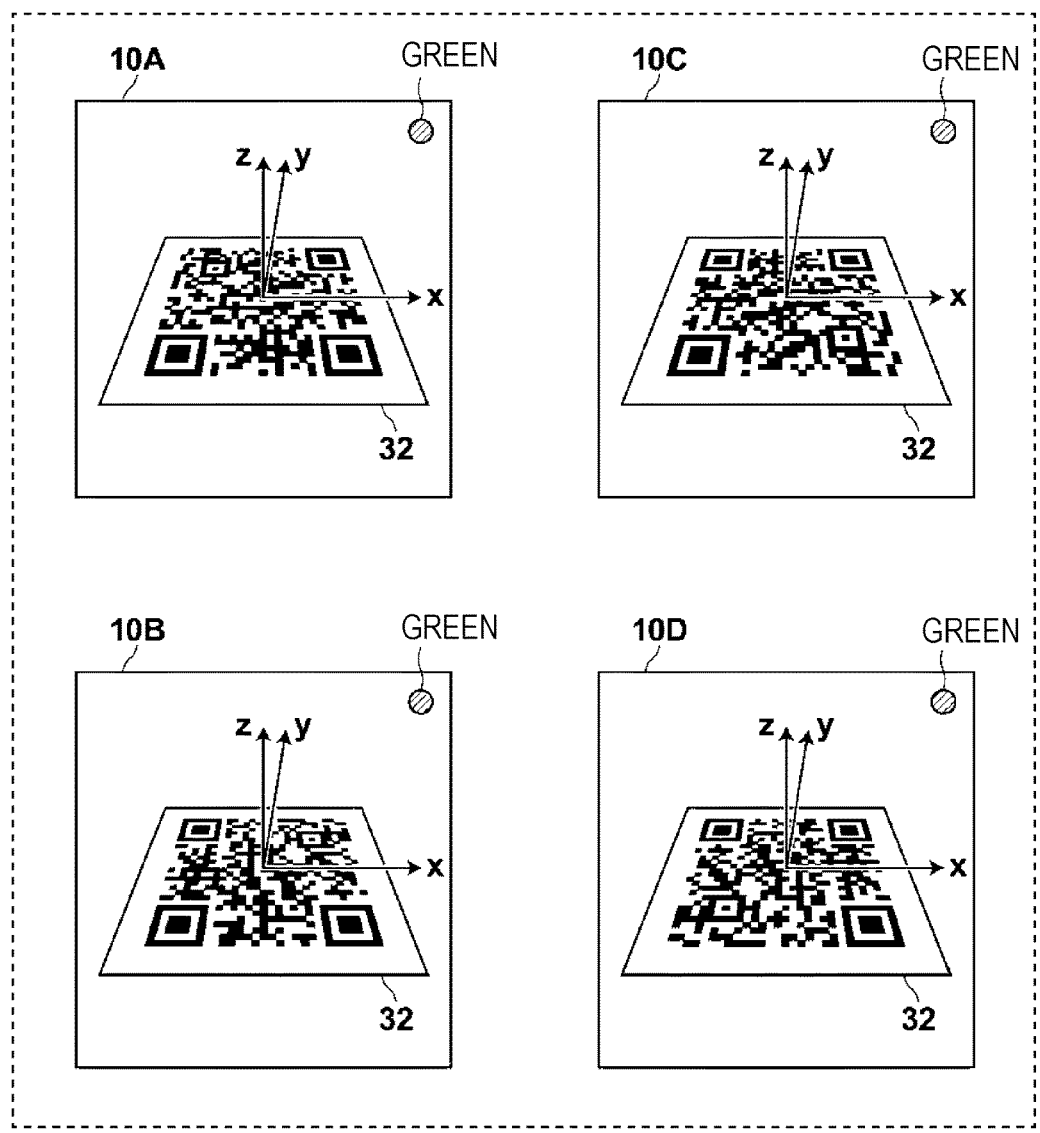
FIG. 7 is a diagram for describing settings of coordinate axes when the mode is switched to a sharing mode.

Upon receipt of the switching instruction signal for switching to the sharing mode, the display control unit 24 of each of the HMDs 1A to 1D registers, as the initial state, a posture of the marker 30 that is imaged by the corresponding one of the HMDs 1A to 1D currently, i.e., at the time of receipt of the switching instruction signal. That is, the display control unit 24 sets, as the initial state, a positional relationship among the reference points 30a, 30b, and 30c of the marker 30 that is imaged currently, and then newly sets coordinate axes of the x direction, the y direction, and the z direction as illustrated in FIG. 7.

Then, immediately before the switching to the sharing mode, display information that has been acquired by the display information acquisition unit 23 of the HMD 1A of the surgeon 31A is output to the HMDs 1B to 1D of the participants 31B to 31D. The display information output from the HMD 1A of the surgeon 31A is then acquired by the display information acquisition unit 23 of each of the HMDs 1B to 1D of the participants 31B to 31D. The display control unit 24 of each of the HMDs 1B to 1D causes the display 15 to display the virtual object S0 on the basis of the acquired display information. That is, the virtual object S0 having an orientation identical to the orientation of the virtual object S0 displayed on the display 15 of the HMD 1A of the surgeon 31A is displayed on the displays 15 of the HMDs 1B to 1D of the participants 31B to 31D.

Note that it is desirable that out of display information representing the size and the orientation in which the virtual object S0 is to be displayed, only information representing the orientation be used as the display information output from the HMD 1A of the surgeon 31A and display information representing the size be excluded when the mode is switched to the sharing mode. It is desirable that the display control unit 24 of each of the HMDs 1B to 1D of the participants 31B to 31D then cause the virtual object S0 to be displayed on the basis of the display information representing the size that is acquired by the display information acquisition unit 23 of the corresponding one of the HMDs 1B to 1D thereof. The reason for this is because more realistic display can be implemented when the size of the virtual object S0 is determined on the basis of the actual positional relationship between the marker 30 and each of the participants 31B to 31D.

Figure 8:
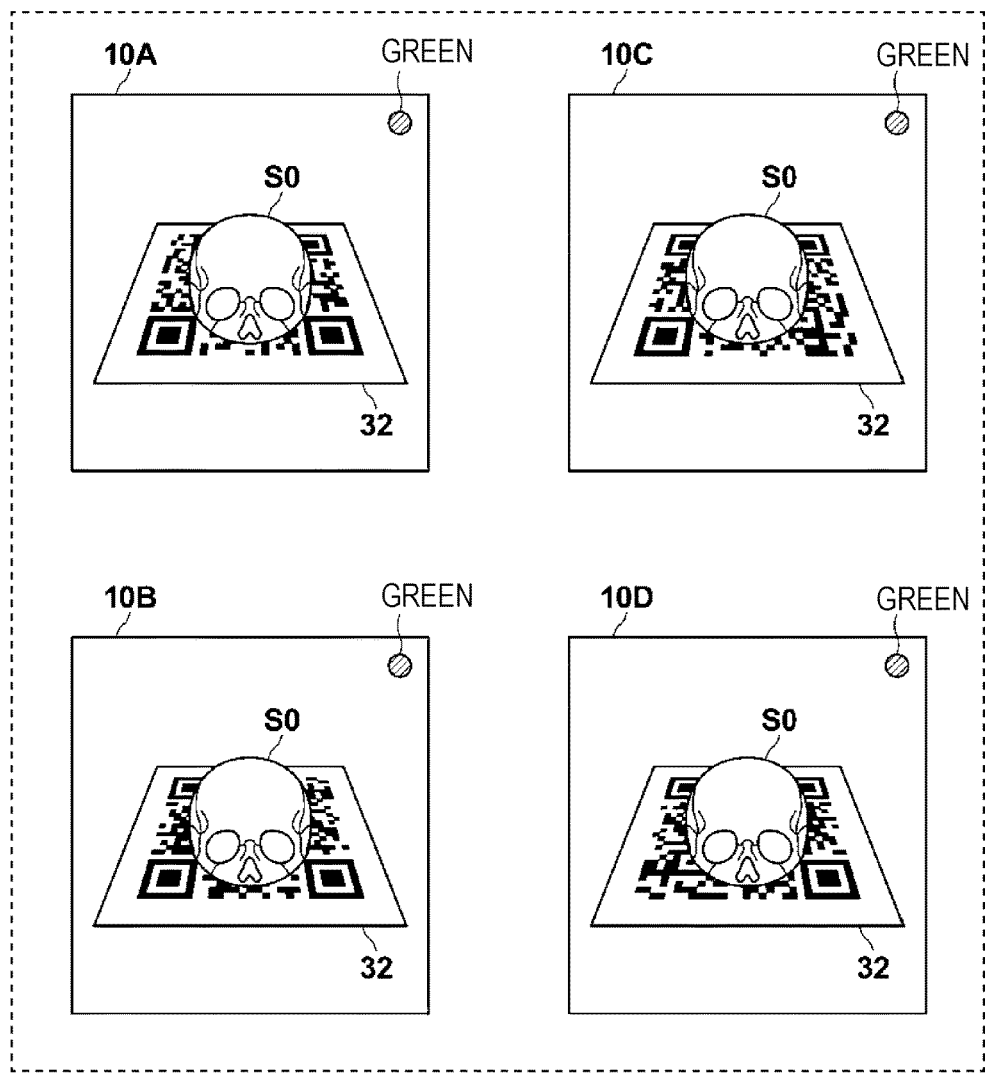
FIG. 8 is a diagram illustrating display states of the virtual object displayed on the individual head-mounted displays in the sharing mode.

FIG. 8 is a diagram illustrating the state of the virtual object S0 displayed on the displays 15 of the HMDs 1A to 1D after the mode has been switched to the sharing mode. As illustrated in FIG. 8, the virtual object S0 having the same orientation can be displayed on the displays 15 of all the HMDs 1A to 1D. In addition, in the sharing mode, a green circular mark indicating that the mode is currently set in the sharing mode is displayed at the upper right corner of the displays 15 of the surgeon 31A and the participants 31B to 31D as illustrated in FIG. 8. Although the red circular mark is displayed in the normal mode and the green circular mark is displayed in the sharing mode in this embodiment as described above, the displayed marks are not limited to these marks. That is, any other display method may be used as long as the display method indicates whether the mode is currently set in the normal mode or in the sharing mode.

In addition, although FIG. 8 illustrates a display example in the case where the virtual object S0 in the front position is displayed on the display 15 of the HMD 1A of the surgeon 31A immediately before the mode is switched to the sharing mode, the position need not necessarily be the front position. For example, in the case where the virtual object S0 viewed diagonally from the right is displayed on the display 15 of the HMD 1A of the surgeon 31A immediately before the mode is switched to the sharing mode, the virtual object S0 viewed diagonally from the right is displayed on the displays 15 of the HMDs 1B to 1D of the participants 31B to 31D after the mode is switched to the sharing mode.

Figure 9:
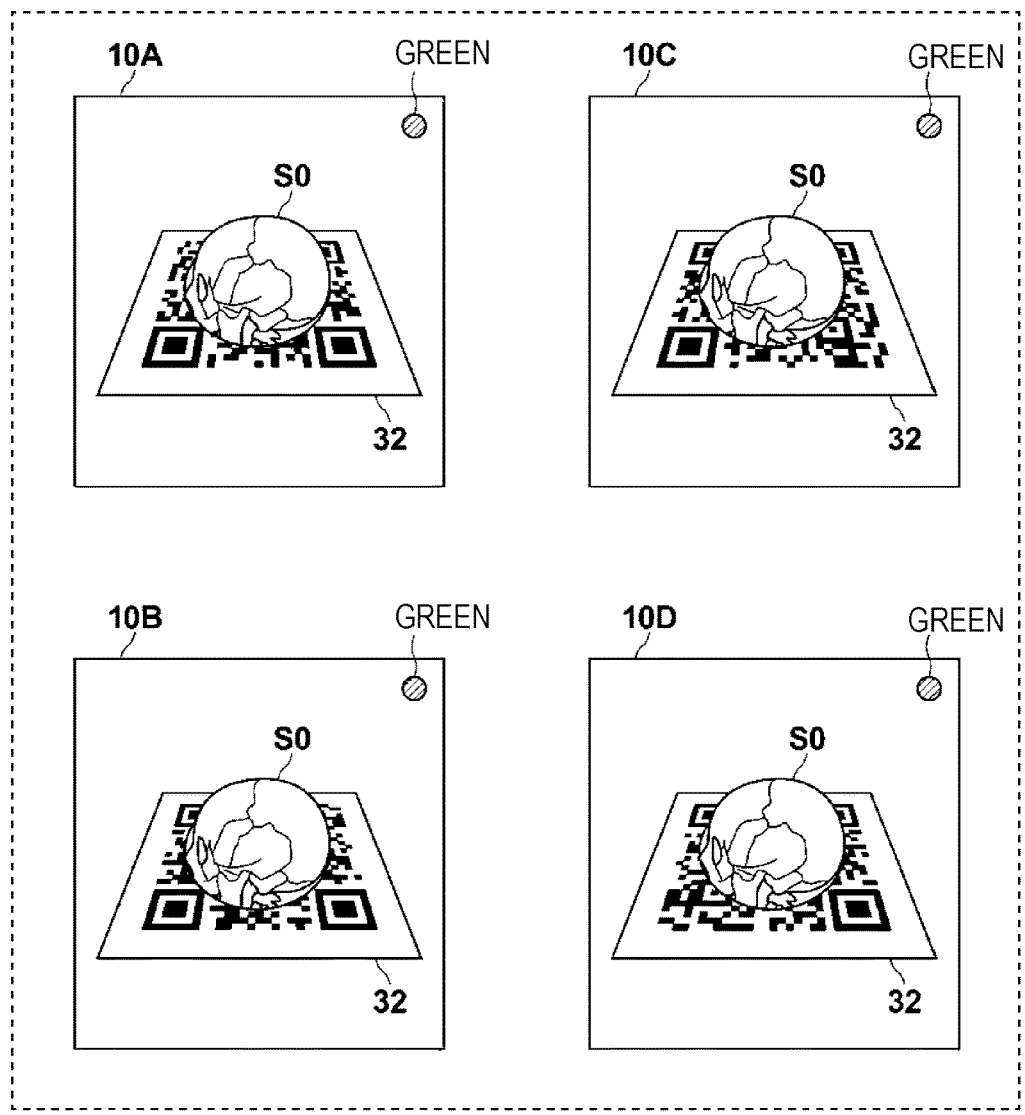
FIG. 9 is a diagram for describing synchronized display of the virtual object in the sharing mode.

Further, in the case where the positional relationship between the surgeon 31A and the marker 30 changes due to movement of the surgeon 31A and consequently the display information acquired by the display information acquisition unit 23 of the HMD 1A of the surgeon 31A is changed after the mode is switched to the sharing mode, the changed display information is output to the HMDs 1B to 1D of the participants 31B to 31D and is acquired by the display information acquisition unit 23 of each of the HMDs 1B to 1D of the participants 31B to 31D. Then, the display control unit 24 of each of the HMDs 1B to 1D of the participants 31B to 31D causes the virtual object S0 to be displayed on the basis of the display information acquired by the display information acquisition unit 23 of the corresponding one of the HMDs 1B to 1D thereof. In this way, the display of the virtual object S0 on the HMDs 1B to 1D of the participants 31B to 31D can be changed in synchronization with the change in the display of the virtual object S0 on the HMD 1A of the surgeon 31A. FIG. 9 illustrates the virtual objects S0 displayed on the displays 15 of the HMDs 1A to 1D in the case where the surgeon 31A has moved to the position of the participant 31B.

Note that also in the case where synchronized display is performed as described above, it is desirable that out of the display information that represents the size and the direction in which the virtual object S0 is to be displayed, only information representing the direction be used as the display information output from the HMD 1A of the surgeon 31A and display information representing the size be excluded.

In addition, in this embodiment, the display of the virtual object S0 on the HMDs 1B to 1D of the participants 31B to 31D is changed in synchronization with the change in the display of the virtual object S0 on the HMD 1A of the surgeon 31A as described above. However, the display of the virtual object S0 on the HMDs 1B to 1D of the participants 31B to 31D may be changed independently by the respective HMDs 1B to 1D instead of performing such synchronized display. That is, the display control unit 24 of each of the HMDs 1B to 1D of the participants 31B to 31D may change the display of the virtual object S0 in accordance with a change in the display information acquired by the display information acquisition unit 23 of the corresponding one of the HMDs 1B to 1D thereof after the mode is switched to the sharing mode.

In addition, the above-described synchronized mode and the independent mode in which synchronization is not performed may be switched between. Switching between the synchronized mode and the independent mode may be performed using the switching controller 50 or may be performed using the input unit 16 of each of the HMDs 1B to 1D of the participants 31B to 31D.

In addition, not only the virtual object S0 but also the background video image B0 may be shared in the sharing mode described above. That is, when the mode is switched to the sharing mode, the background video image B0 captured by the camera 14 of the HMD 1A of the surgeon 31A may be output to the HMDs 1B to 1D of the participants 31B to 31D. Then, the display control unit 24 of each of the HMDs 1B to 1D of the participants 31B to 31D may superimpose the virtual object S0 not on the background video image B0 captured by the camera of the corresponding one of the HMDs 1B to 1D thereof but on the background video image B0 captured by the camera 14 of the HMD 1A of the surgeon 31A and may display the resultant combined image on the display 15.

Note that a configuration may be made so that a background-not-sharing mode in which the background video image B0 is not shared, that is, the display control unit 24 of each of the HMDs 1B to 1D of the participants 31B to 31D superimposes the virtual object S0 on the background video image B0 captured by the camera of the corresponding one of the HMDs 1B to 1D thereof and displays the resultant combined image on the display 15 and the above-described background sharing mode in which the background video image B0 is shared can be switched between. Note that the background-not-sharing mode corresponds to third display control according to an aspect of the present invention, and the background-sharing mode corresponds to fourth display control according to an aspect of the present invention. Switching between the background-not-sharing mode and the background-sharing mode may be performed using the switching controller 50 or may be performed using the input unit 16 of each of the HMDs 1B to 1D of the participants 31B to 31D.

Figure 10:
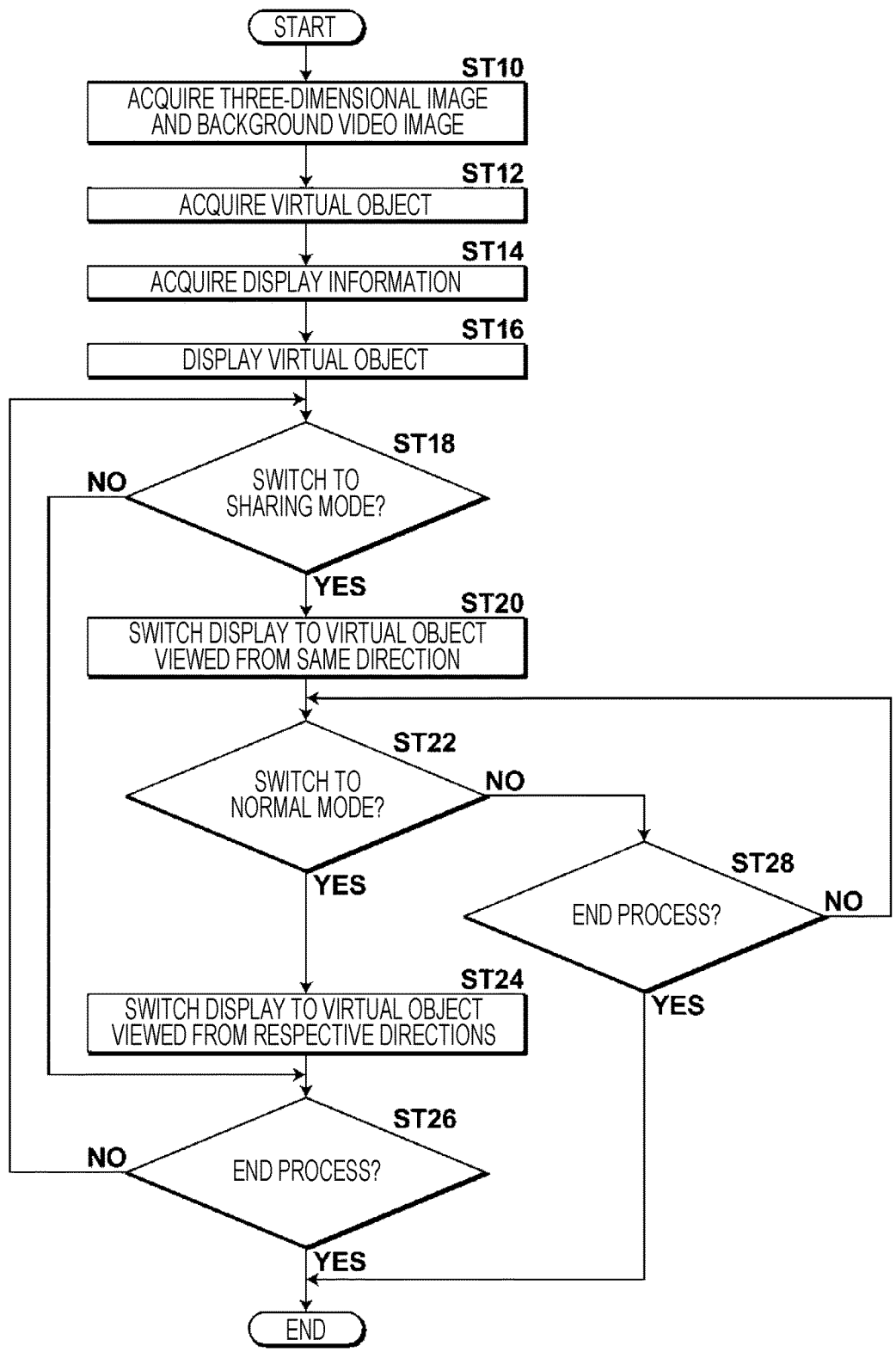
FIG. 10 is a flowchart for describing an operation of the embodiment of the virtual object display system according to the aspect of the present invention.

An operation of the virtual object display system according to this embodiment will be described next with reference to a flowchart illustrated in FIG. 10.

First, the image acquisition unit 21 of each of the HMDs 1A to 1D acquires the three-dimensional image V0 and the background video image B0 (step ST10). The virtual object acquisition unit 22 acquires the virtual object S0 from the three-dimensional image V0 (step ST12). In addition, the display information acquisition unit 23 of each of the HMDs 1A to 1D extracts the marker image 32 representing the marker 30 from the background video image B0 and acquires, from the marker image 32, display information representing the position at which and the size and orientation in which the virtual object S0 is to be displayed (step ST14). Then, the display control unit 24 of each of the HMDs 1A to 1D superimposes the virtual object S0 on the background video image B0 and displays the resultant combined image on the display 15 by using the display information (step ST16). Consequently, the surgeon 31A and the participants 31B to 31D of the pre-surgery conference who are wearing the HMDs 1 can observe the state where the virtual object S0 is displayed in the real space.

Then, if the surgeon 31A gives an instruction for switching to the sharing mode by using the switching controller 50 in the state of the normal mode described above (YES in ST18), the mode is switched to the sharing mode described above. In the sharing mode, the virtual object S0 having an orientation identical to the orientation of the virtual object S0 displayed on the display 15 of the HMD 1A of the surgeon 31A is displayed on the displays 15 of the HMDs 1B to 1D of the participants 31B to 31D (ST20).

Then, if the surgeon 31A gives an instruction for switching to the normal mode by using the switching controller 50 in the state of the sharing mode (YES in ST22), the mode is switched to the normal mode, and the virtual object S0 based on the positional relationship between the marker 30 and each of the participants 31B to 31D, that is, the virtual object S0 having an orientation according to the position of each of the participants 31B to 31D, is displayed on the display 15 of the corresponding one of the HMDs 1B to 1D of the participants 31B to 31D (ST24).

If an instruction for ending the process is given (YES in ST26) without switching the mode to the sharing mode in ST18 (NO), if an instruction for ending the process is given (YES in ST28) without switching the mode to the normal mode in ST22 (NO), and if an instruction for ending the process is given (YES in ST26) after the mode is switched to the normal mode, the process is ended without any further processing.

With the virtual object display system according to the embodiment described above, in the case where a common virtual object is displayed on the plurality of HMDs 1, the normal mode in which the virtual object is displayed on the basis of display information acquired by each of the plurality of HMDs 1 and the sharing mode in which the virtual object having an orientation identical to the orientation of the virtual object that is displayed on the basis of the display information acquired by another HMD 1 is displayed is switched between. Since the normal mode in which each observer can view the common virtual object from the direction of the observer and the sharing mode in which other observers can observe the virtual object from the direction identical to the direction in which, for example, the surgeon views the virtual object can be switched between, each observer can observe the virtual object from an appropriate direction according to a situation without moving.

Figure 11:
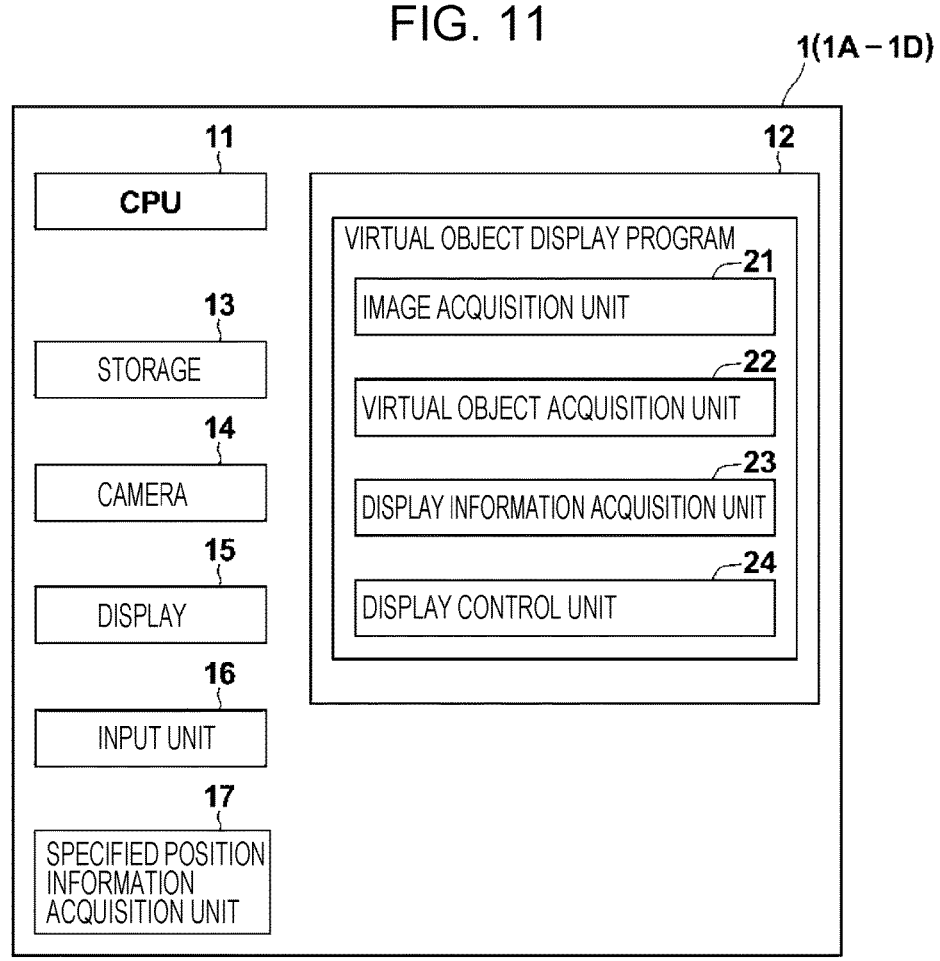
FIG. 11 is a block diagram illustrating another embodiment of a head-mounted display which is a virtual object display device.
Figure 12:
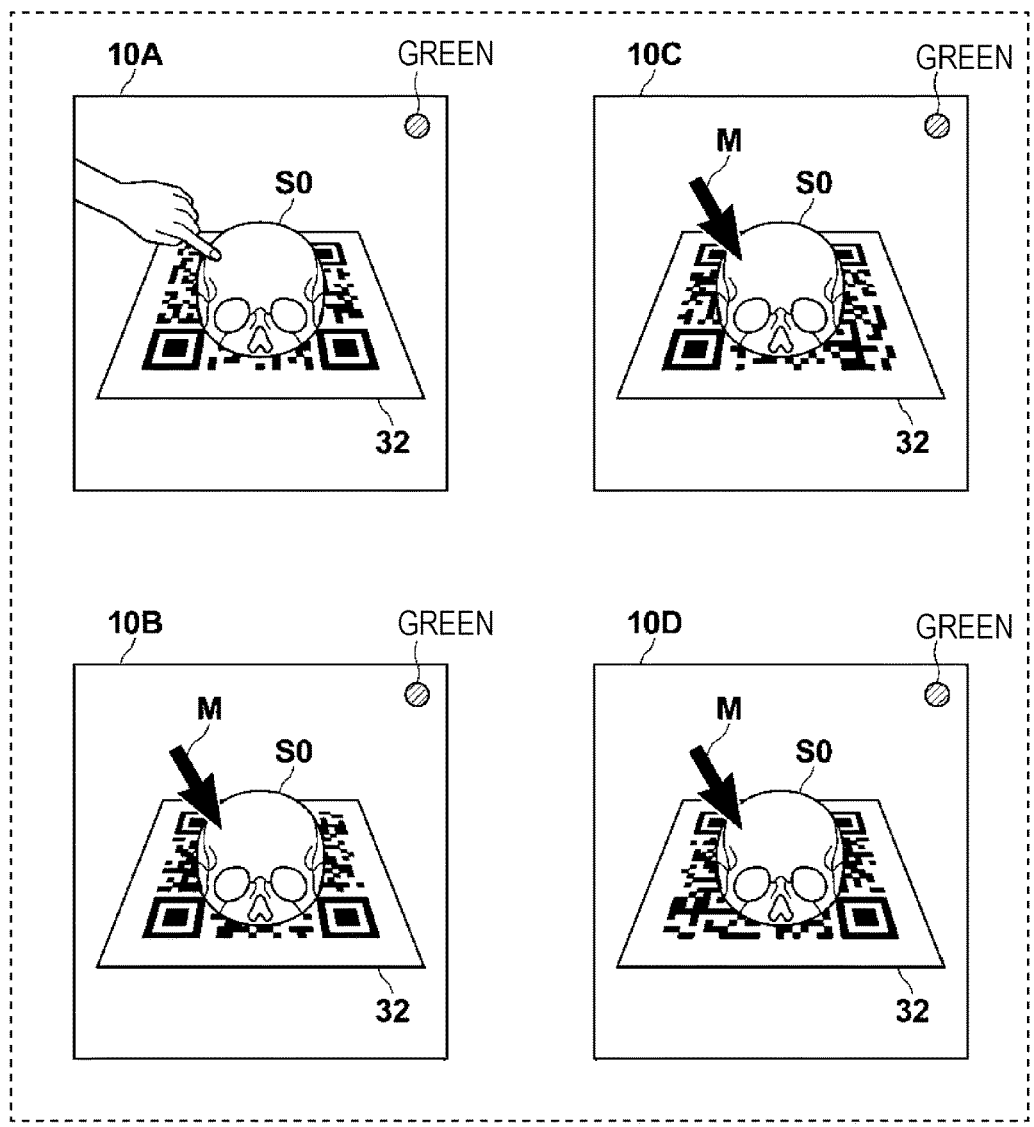
FIG. 12 is a diagram for describing an example in which an image representing a position specified on the virtual object is displayed on the virtual object on the basis of information on the specified position in the sharing mode.

In addition, in the virtual object display system according to the embodiment described above, a specified position information acquisition unit 17 may be further provided as illustrated in FIG. 11. When a position on the virtual object S0 is specified with a finger by the surgeon 31A in the sharing mode as illustrated in FIG. 12, the specified position information acquisition unit 17 acquires position information on the specified position. Then, the display control unit 24 of each of the HMDs 1B to 1D of the participants 31B to 31D may cause an arrow image M that represents the specified position on the virtual object displayed on the display 15 thereof to be displayed on the basis of the position information acquired by the specified position information acquisition unit 17. Since the participants 31B to 31D can grasp the position on the virtual object S0 pointed by the surgeon 31A with a finger in this way, the participants 31B and 31D can clearly know the part which the surgeon 31A is currently focusing on. Note that the displayed image is not limited to the arrow image, and another mark or the like may be used.

For example, a three-dimensional position sensor or the like can be used as the specified position information acquisition unit 17. Alternatively, the position of the end of the finger may be detected based on the background video image B0, and the specified position information may be acquired based on a positional relationship among the end position and the reference points 30a, 30b, and 30c of the marker image 32.

In addition, although the surgeon 31A specifies a position on the virtual object S0 with a finger in the above description, an object to be used is not limited to a finger and the position may be specified by using another object, such as a pen or a pointer.

In addition, in the embodiments described above, the surgeon 31A operates the switching controller 50, whereby the normal mode and the sharing mode are switched between. However, a person who operates the switching controller 50 is not limited to the surgeon 31A, and the other participants 31B to 31D may operate the switching controller 50. In this case, for example, the switching controller 50 may recognize the HMD 1 that is located closest to the switching controller 50, and the virtual object S0 having an orientation identical to the orientation of the virtual object S0 displayed on the closest HMD 1 may be displayed on the other HMDs 1.

Further, switching between the normal mode and the sharing mode may be accepted via the input unit 16 of each of the HMDs 1. In this case, for example, the virtual object S0 having an orientation identical to the orientation of the virtual object S0 displayed on the HMD 1 to which the input unit 16 that has accepted input of the switching instruction belongs may be displayed on the other HMDs 1.

In addition, in the embodiments described above, a marker obtained by sticking a two-dimensional barcode to a plate is used. However, a predetermined symbol, color, drawing, character, or the like may be used instead of the two-dimensional barcode. In addition, the marker may be a predetermined object, such as an LED, a pen, or an operator's finger. Further, an intersection of lines included in the background video image B0 or a texture of a shining object or the like may be used as the marker.

In addition, in the embodiments described above, the HMD 1 is equipped with the camera 14. However, the camera 14 may be provided separately from the HMD 1. Also in this case, the camera 14 is preferably arranged to image the range corresponding to the field of view of the wearer of the HMD 1.

In addition, in the embodiments described above, the virtual object display device according to an aspect of the present invention is applied to an HMD, which is an immersive-type eyeglass-shaped display device. However, the virtual object display device according to the aspect of the present invention may be applied to a see-through-type eyeglass-shaped terminal device. In this case, the display 15 is a see-through type display, and as a result of displaying the virtual object S0 on the display 15, the wearer of the virtual object display device can observe the virtual object S0 superimposed on the real space which the wearer is actually viewing, instead of the background video image B0 that is captured by the camera 14 and is displayed on the display 15. In addition, in this case, the camera 14 is used to image the marker 30 used for determining the position at which and the size in which the virtual object S0 is to be displayed.

In addition, in the embodiments described above, the virtual object display device according to an aspect of the present invention is applied to an eyeglass-shaped display device. However, the virtual object display device according to the aspect of the present invention may be applied to a camera-equipped tablet terminal. In this case, the surgeon 31A and the participants 31B to 31D carry their tablet terminals, and the background video image B0 and the virtual object S0 are displayed on the displays of the tablet terminals.

In addition, in the embodiments described above, the position at which and the orientation in which the virtual object S0 is to be displayed may be used as the display information. In this case, the virtual object S0 having a predetermined size may be displayed on the display 15.

In addition, although the virtual object S0 generated from a three-dimensional medical image is displayed in the embodiments described above, the type of the virtual object S0 is not limited to a medical object. For example, a game character, a model, or the like may be used as the virtual object S0.

REFERENCE SIGNS LIST 1 head-mounted display
2 three-dimensional imaging apparatus
3 image storage server
4 network
12 memory 13 storage
14 camera
15 display
16 input unit
17 specified position information acquisition unit
21 image acquisition unit
22 virtual object acquisition unit
23 display information acquisition unit
24 display control unit
30 marker
32 marker image
50 switching controller
51 mode switching button

What is claimed is:

1. A virtual object display system comprising:
a plurality of virtual object display devices each having a processor configured to acquire a virtual object, acquire display information including position information used to display the virtual object and orientation information used to display the virtual object, and cause a display unit to display the virtual object on the basis of the display information,
wherein the processor of each of the plurality of virtual object display devices is capable of switching between first display control for causing the virtual object to be displayed on the basis of display information acquired by the processor of the virtual object display device and second display control for causing the virtual object having an identical orientation to an orientation of the virtual object displayed on the basis of display information acquired by the processor of another virtual object display device among the plurality of virtual object display devices to be displayed, and
wherein in a case where the display information acquired by the processor of the other virtual object display device is changed after switching to the second display control, the processor of each of the plurality of virtual object display devices changes display of the virtual object on the basis of the changed display information.

2. The virtual object display system according to claim 1, wherein
the display information includes size information used to display the virtual object, and
in a case where the display information acquired by the processor of the other virtual object display device is changed after switching to the second display control, the processor of each of the plurality of virtual object display devices changes display of the virtual object on the basis of the changed display information excluding the size information.

3. The virtual object display system according to claim 1, wherein the processor of each of the plurality of virtual object display devices changes display of the virtual object in accordance with a change in the display information acquired by the processor of the virtual object display device after switching to the second display control.

4. The virtual object display system according to claim 1, wherein
each of the plurality of virtual object display devices comprises an imaging unit that acquires a background video image, and
the processor of each of the plurality of virtual object display devices
in a case of the first display control, causes the background video image acquired by the imaging unit of the virtual object display device and the virtual object to be displayed and superimposed, and
in a case of the second display control, is capable of switching between third display control for causing the background video image acquired by the imaging unit of the virtual object display device and the virtual object having the identical orientation to be displayed and superimposed and fourth display control for causing the background video image acquired by the imaging unit of the other virtual object display device and the virtual object having the identical orientation to be displayed and superimposed.

5. The virtual object display system according to claim 2, wherein
each of the plurality of virtual object display devices comprises an imaging unit that acquires a background video image, and
the processor of each of the plurality of virtual object display devices
in a case of the first display control, causes the background video image acquired by the imaging unit of the virtual object display device and the virtual object to be displayed and superimposed, and
in a case of the second display control, is capable of switching between third display control for causing the background video image acquired by the imaging unit of the virtual object display device and the virtual object having the identical orientation to be displayed and superimposed and fourth display control for causing the background video image acquired by the imaging unit of the other virtual object display device and the virtual object having the identical orientation to be displayed and superimposed.

6. The virtual object display system according to claim 1, the processor further configured to:
acquire, after a position on the virtual object displayed on a virtual object display device among the plurality of virtual object display devices is specified by a user, position information on the specified position,
wherein the processor of the virtual object display devices other than the virtual object display device associated with the user who has specified the position on the virtual object causes an image representing the specified position to be displayed on the virtual object on the basis of the position information acquired by the processor.

7. The virtual object display system according to claim 2, the processor further configured to:
acquire, after a position on the virtual object displayed on a virtual object display device among the plurality of virtual object display devices is specified by a user, position information on the specified position,
wherein the processor of the virtual object display devices other than the virtual object display device associated with the user who has specified the position on the virtual object causes an image representing the specified position to be displayed on the virtual object on the basis of the position information acquired by the processor.

8. The virtual object display system according to claim 1, the processor further configured to:
accept a switching instruction for switching between the first display control and the second display control,
wherein the processor of each of the plurality of virtual object display devices switches between the first display control and the second display control in accordance with the switching instruction accepted by the switching instruction accepting device.

9. The virtual object display system according to claim 2, the processor further configured to:
accept a switching instruction for switching between the first display control and the second display control,
wherein the processor of each of the plurality of virtual object display devices switches between the first display control and the second display control in accordance with the switching instruction accepted by the switching instruction accepting device.

10. The virtual object display system according to claim 1, wherein the processor acquires the display information from a marker image obtained by imaging a marker used to display the virtual object.

11. The virtual object display system according to claim 2, wherein the processor acquires the display information from a marker image obtained by imaging a marker used to display the virtual object.

12. The virtual object display system according to claim 1, wherein the virtual object is a three-dimensional image.

13. The virtual object display system according to claim 12, wherein the three-dimensional image is a three-dimensional medical image.

14. The virtual object display system according to claim 1, wherein the virtual object is a three-dimensional image.

15. The virtual object display system according to claim 14, wherein the three-dimensional image is a three-dimensional medical image.

16. The virtual object display system according to claim 1, wherein the display unit is an eyeglass-shaped display device.

17. The virtual object display system according to claim 1, wherein the display unit is an eyeglass-shaped display device.

18. A display control method for a virtual object display system, the virtual object display system comprising a plurality of virtual object display devices each of which acquires a virtual object, acquires display information including position information used to display the virtual object and orientation information used to display the virtual object, and causes a display unit to display the virtual object on the basis of the display information,
wherein each of the plurality of virtual object display devices switches between first display control for causing the virtual object to be displayed on the basis of display information acquired by the virtual object display device and second display control for causing the virtual object having an identical orientation to an orientation of the virtual object displayed on the basis of display information acquired by another virtual object display device among the plurality of virtual object display devices to be displayed, and
wherein in a case where the display information acquired by the other virtual object display device is changed after switching to the second display control, each of the plurality of virtual object display devices changes display of the virtual object on the basis of the changed display information.

19. A non-transitory computer readable recording medium storing a display control program for a virtual object display system, the virtual object display system comprising a plurality of virtual object display devices each of which acquires a virtual object, acquires display information including position information used to display the virtual object and orientation information used to display the virtual object, and causes a display unit to display the virtual object on the basis of the display information,
the display control program causing each of the plurality of virtual object display devices to execute a process of switching between first display control for causing the virtual object to be displayed on the basis of display information acquired by the virtual object display device and second display control for causing the virtual object having an identical orientation to an orientation of the virtual object displayed on the basis of display information acquired by another virtual object display device among the plurality of virtual object display devices to be displayed
wherein in a case where the display information acquired by the other virtual object display device is changed after switching to the second display control, each of the plurality of virtual object display devices changes display of the virtual object on the basis of the changed display information.

* * * * *